United States Patent
Varona

(10) Patent No.: US 10,559,287 B2
(45) Date of Patent: Feb. 11, 2020

(54) STRINGED MUSICAL INSTRUMENT ADJUSTABLE NECK JOINT

(71) Applicant: Ray Varona, Charlottesville, VA (US)

(72) Inventor: Ray Varona, Charlottesville, VA (US)

(73) Assignee: Damman Custom Instruments LLC, Charlottesville, VA (US)

( * ) Notice: Subject to any disclaimer, the term of this patent is extended or adjusted under 35 U.S.C. 154(b) by 0 days.

(21) Appl. No.: 15/937,846

(22) Filed: Mar. 27, 2018

(65) Prior Publication Data

US 2018/0218717 A1 Aug. 2, 2018
US 2019/0139517 A9 May 9, 2019

Related U.S. Application Data

(60) Provisional application No. 62/477,059, filed on Mar. 27, 2017.

(51) Int. Cl.
| | |
|---|---|
| *G10D 3/06* | (2006.01) |
| *A61J 1/20* | (2006.01) |
| *A61J 1/18* | (2006.01) |
| *A61J 1/14* | (2006.01) |
| *G10D 1/08* | (2006.01) |

(52) U.S. Cl.
CPC .............. *G10D 3/06* (2013.01); *A61J 1/1406* (2013.01); *A61J 1/18* (2013.01); *A61J 1/2055* (2015.05); *A61J 1/2096* (2013.01); *A61J 2205/20* (2013.01); *G10D 1/08* (2013.01)

(58) Field of Classification Search
CPC ............ G10D 1/08; G10D 3/06; A61J 1/2065
See application file for complete search history.

(56) References Cited

U.S. PATENT DOCUMENTS

| | | | |
|---|---|---|---|
| 7,157,634 B1* | 1/2007 | Babicz | G10D 3/06 84/267 |
| 2016/0027415 A1* | 1/2016 | Hooker | G10D 3/06 84/293 |

* cited by examiner

*Primary Examiner* — Kimberly R Lockett
(74) *Attorney, Agent, or Firm* — Woods Rogers PLC; Nathan A. Evans

(57) ABSTRACT

An adjustable neck system for ease of action adjustment within a wide range of possible string heights and vibrating string lengths while not impeding on the vibrating area of the soundboard and adding minimal mass to the headblock assembly and allowing for significant rigidity to allow for greatly improved tuning stability is described. The system includes a neck joint utilizing a neck that pivots into a slightly mortised headblock with a floating, cantilevered fingerboard that does not contact the surface of the soundboard. The neck heel features extensive reinforcement in conjunction with headblock reinforcement to allow for increased torque on between the captive bolts and pivot points for greater rigidity and stability without the need for locking screws. By laminating the headblock and cantilevering the fingerboard, mass and soundboard contact area is not significantly greater than with traditional assemblies for minimal effect on weight balance and tone.

21 Claims, 14 Drawing Sheets

Instrument Top

Instrument Side

STRINGED MUSICAL INSTRUMENT ADJUSTABLE NECK JOINT

CROSS-REFERENCE TO RELATED APPLICATIONS

The present application relies on the disclosures of and claims priority to and the benefit of the filing date of U.S. Provisional Application Nos. 62/477,059, filed Mar. 27, 2017. The disclosures of that application are hereby incorporated by reference herein in their entireties.

BACKGROUND

Field of the Invention

The present invention relates to the neck joint on stringed musical instruments, particularly to one that enables the user to adjust the string and fingerboard geometry to facilitate ease of play by means of controlling the neck angle about a pivot point.

Description of the Related Art

While stringed instruments are initially designed and built with geometries that provide for a comfortable playing height between the strings and playing surface, the long-term effects of string tension create distortions in the instrument that have a negative effect on the playing height and original design parameters. For optimum tonal response, instruments are built with very little safety factor for the structural loads they must bear and, in most cases, the instrument begins to buckle as the two opposing points of the strings, typically a nut on a neck and a bridge or tailpiece on a body, pull towards each other. The net effect is a raising of the height between the strings and the fingerboard, making the instrument more difficult to play than originally intended. This also has the additional undesirable side effect of shortening the vibrating string length which requires an increase between the points to compensate. This presents a particular problem with fixed-bridge instruments where the only means of moving the vibrating string length is to reshape the bridge or, in most cases, provide a relatively thin, removable strip of bone or other hard material referred to as a saddle that is seated in a matching slot grooved into the fixed bridge. The intonation is corrected by filing an angle into the saddle, provided that there is enough thickness in the saddle to effectively ramp the intonation point back. If this cannot be done the saddle slot must be filled with wood and the slot re-routed at a position further back. To address playing height, the bridge can be cut down in height, although sufficient height might not be available in many instances and bridge height, mass, and stiffness are all important aspects of bridge design and modifying any of these parameters most likely changes the tone in unwanted ways. Instead of modifying the bridge, instruments facing significant deformation can have their action restored by means of a procedure known as a neck reset where the neck is separated from the body, trimmed, and shimmed to move the neck angle backwards. After gluing the neck back into position, fretted instruments would require additional fret leveling and reshaping to address the change in the fingerboard to body junction. The act of separating the neck typically carries the risk of damage during the removal process and often requires minor finish repair. While neck resets are a commonplace procedure particularly for guitars and flat-top fretted instruments after 2-3 decades of use, it is still regarded as the equivalent of major surgery to an instrument if the neck joint was constructed with traditional techniques such as a glued dovetail joint or integral, slotted neck or Spanish heel. Violin family and most other instruments also typically require neck resets over time, though not as early or often. Necks utilizing threaded bolts with simplified joints such as a butt or mortise and tenon are rapidly becoming commonplace as seen in Taylor, Goodall, and Collings guitars. While these bolt-on necks eliminate the need for steaming, a skilled luthier or technician is still required to set the neck properly and these joints require disassembly of the neck joint to perform an adjustment.

Apart from long-term deformation, playing action is also susceptible to change over the short-term from fluctuations in humidity which cause the wooden components of the instrument to swell or shrink in response. With increments as small as 0.01" creating noticeable changes in playability, without any integrated adjustment mechanisms the only short-term fix is to change or recut the bridge or in the case of fixed-bridges utilizing a saddle, either shim or shave the saddle to account for these fluctuations. Changing the saddle or swapping a bridge requires loosening the strings and is considered largely impractical for end-users as a daily means of adjustment and any fine-tuning requires sanding or shimming of the saddles which is often considered a task for a luthier or technician. Typical practice is to have a taller bridge or saddle for the drier periods in winter and a shorter counterpart for the humid conditions in summer as a compromise.

Several solutions have been developed to allow for easier vertical adjustment at the bridge, such as Gibson musical instrument's early screw-adjustable saddles from the 1950's to a number of modern patent applications and patents, such as U.S. Patent Application No. 2016/0098976 and U.S. Pat. No. 7,488,878. All patents and patent applications mentioned herein are incorporated by reference.

The lack of widespread adaptation of Gibson's adjustable saddle illustrates the finding that additional mass to the bridge has a damping effect on the tone quality of an instrument. Bowed stringed instruments routinely use small weights clipped onto the top of the bridge as mutes and while not as pronounced on fixed-bridge instruments, addition of significant mass without any benefits to stiffness tend to be detrimental to tonal goals. Designs that utilize additional metal elements or a larger saddle apparatus (e.g., U.S. Patent Application No. 2016/0098976 and U.S. Pat. No. 7,488,878) present a compromise to tone while only providing slight action adjustment which would likely only account for seasonal changes and not the extensive changes from time-induced deformation. The materials traditionally selected for use in bridges and saddles fall within a specific range of density, stiffness, and damping characteristics and have a significant influence on the tonal character as the primary coupling point between the strings and the resonating body of the instrument. Most adjustable saddles utilizing threaded metal components potentially introduce unwanted material characteristics at one of the most critical points in the instrument's kinetic chain, requiring significant changes to the overall instrument design if achieving commonly accepted tonal designs are sought. Adjustable saddles also provide little to no control of string compensation length so this method of correction only solves part of the problems while bringing the primary criteria of an instrument, tone production, into question.

Addressing the action by either allowing for a rotating neck or changing the elevation of the neck has existing implementations. Adjustment of neck angle by means of tilting is a concept that is commonly first attributed to 19th century, gut-strung classical guitars of the Romantic period (approx. 1830-1840) with Viennese builders such as Johann Stauffer and C. F. Martin Sr., and then later rediscovered and now implemented by a number of notable contemporary luthiers such as Thomas Rein, Mike Doolin, Mike Baranik, Rick Turner, Gary Southwell. An existing patent application addresses adjustability by allowing for the tracking of the neck vertically; the Babicz continually-adjustable neck system: U.S. Patent Application No. 2007/0107579 A1 as well as contemporary solutions in the case of Ken Parker's adjustable archtop neck.

The historic design of a tilt-adjustable neck as developed by Stauffer and continued by Martin utilizes a threaded bolt that runs through the lower portion of the heel into the headblock of the instrument. String tension pulled the back of the neck heel into contact with the headblock and the length of the bolt allows a controlled amount of space between the bottom of the heel and headblock, increasing the neck angle with extension of the bolt and decreasing the neck angle with contraction. While this design was highly novel at the time when the standard approach to a neck joint consisted of a fixed, glued, dovetail, the design ceased to continue following Stauffer's career and Martin began to discontinue the neck joint starting in the 1850s until reverting entirely to dovetailed joints by the late 1800s. No primary sources offer a decisive reason but general consensus is that this implementation suffers from a lack of geometric and pitch stability. With the normal force exerted by string tension serving as the main stabilizing force, the relatively low-tension from gut strings of this period would make for a neck that is relatively easy to shift in place with common forces exerted in the process of playing. Modern attempts at adapting a pivoting neck are geared towards developing a design that can withstand the additional tension of modern steel strings (over double in the case of classical guitar versus steel string sets) while overcoming the stability problem of the original design.

Most of the modern adaptations of the tilting neck have some drawbacks due to a number of design choices including utilization of a mortised pocket for the neck extension in the soundboard and/or relatively large neck blocks, locking screws that must be loosened or tightened from the inside of the instrument meant to limit unwanted freedom of movement, and reliance of tightness of fit between joints to achieve rigidity and stiffness. Current implementations of a tilting neck concept such as U.S. Patent Application No. 2016/0027415 feature many of these limitations, complications and drawbacks.

Physical balance for an acoustic stringed instrument is highly sensitive to the distribution of mass and the additional weight from designs featuring a fingerboard extension pocket, enlarged neck block, or large pieces of metallic hardware can negatively affect the balance as well as possibly having a damping effect on the soundboard in the case of a recessed pocket for the fingerboard extension. Many of the modern implementations feature an enlarged head block to accommodate a mortise assembly. This mortise allows for the neck to translate through a range of motion that passes through the plane of the soundboard, without the soundboard actually impeding movement. In fixed-position bolt-on necks this mortise provides an attachment point for lateral stability and some implementations of a tilting neck use a tightly-fitting joint between the fingerboard extension and the body mortise to achieve similar rigidity. By comparison, a traditional approach with a dovetail joint or non-mortised butt joint uses a smaller headblock and a spruce cross-grain brace (or braces) for much less mass. In addition to shifting the center of gravity towards the neck slightly (generally seen as a negative effect and referred to pejoratively as "neck-dive"), the overall increase in weight carries negative perceptions of an "overbuilt" guitar, whereas lighter instruments are perceived to be more "lively" and finely built. Additionally, having the added mass coupled with a typically two-fold (or more) increase in surface area results in significant damping in the upper bout effectively diminish the total free vibrating surface area of the soundboard with negative tonal effects.

A neck that is free to pivot is also prone to minute fluctuations in vibrating string length, which in turn causes unwanted fluctuations in pitch. This phenomenon is akin to the tuning stability problems in a spring-countered bridge assembly such as those seen on Fender Stratocaster or Bigsby tremolos. Some designs add additional screws to provide multiple contact points to add stability to the neck assembly, although these screws must be loosened and tightened with each adjustment. The adjustment points for the screws are typically located inside the body of the instrument with the strings impeding easy access, making fine-tuning more inconvenient. Solutions that utilize a primary pivot screw rely on string tension to counter backwards pull to the neck but can still exhibit pitch sharpening due to backwards pull from the fretting hand unless the pivot screw is fixed in position. If the screw is captive by gluing into place between wooden members or closure with a plug this presents added complication in the event of a repair.

In addition to potential unwanted movement in the vertical direction (or rotation about the axis of the pivot line), most pivoting necks offer little protection against unwanted lateral movement (or rotation about the neck joint when viewed from the top). This movement is most commonly expressed by either straps that are fixed to the headstock and endpin, producing an upward torque on the neck (relative to playing position), or the downward component of pressure from the fretting arm, producing a downward torque on the neck. Despite string tension and connector tension working to counter this torque, the leverages are in favor of unwanted rotation, especially when minimal movement of the pivot point translates to significant error to the neck angle and alignment. A traditional instrument with the fingerboard extension glued down to the soundboard provides rigidity against these moments as does a snugly-fitting mortise that seats the fingerboard extension but short of additional constraints, a pivoting neck relies on the span of contact at its pivot point and the normal force holding the neck fast to the pivot.

Since the width of the heel is fixed, the remaining ways to offset lateral torque are to either dramatically increase the normal force at the pivot point or add a movable third contact point at the fingerboard extension to provide lateral stability though not without further complication. With the wooden components in an instrument, the yield strength of wood ultimately becomes a limiting factor. Current implementations involve reinforcing the heel at the contact point with metal disc inserts and/or metal inserts in the headblock. Metal inserts can provide local stiffness but do not address the reinforcement of the heel throughout its length. Between the normal force from string tension at the pivot and the attachments in the lower section of a heel, the resulting bending moment is applied through a section of endgrain in the heel, which the inserts do not address. Common practice involves gluing wooden dowels down through the heel to reinforce the end grain in a perpendicular manner, though heels reinforced in this manner may still crack with the dowels only serving to prevent complete separation of the heel. In some rare cases, the differential expansion of the captive dowels and the heel can even contribute to cracking of the heel if used in sufficient size to provide adequate reinforcement which often occupies a significant amount of cross-sectional area.

While tight-fitting joinery is a hallmark of fine woodworking, for surfaces that must move freely the associated binding that can occur due to swelling of dimensions in response to humidity can lead to imprecise adjustment (as illustrated by ill-turning violin pegs). The tight fitting helps to provide stability against the side-to-side rotation of the neck but compromises the primary advantage of the adjustable neck. Additionally, any mortised area that is tight enough to rub can cause a number of blemishes in the film finishes including imprinting, blistering, and de-lamination.

The anchoring of the inserts is another potential point of localized yielding or complete fracture and failure of the heel. Traditionally, lightweight hardwoods such as Mahogany or Spanish Cedar have been used for the headblock since the load of string tension was distributed over a relatively large surface area. Those same woods offer limited strength for holding threads as well as compression on face grain (headblocks are not oriented with endgrain facing the neck). Common solutions are brass inserts with larger, coarser threads or using large setscrews to form the pivot points. With the common headblock grain orientation running parallel to the line of pivot, increasing the size of the screws and inserts increases the likelihood of splitting as the cross sectional area directly in line with stress is reduced by the enlargement of the pivot points. Additionally, over time the combination of wood shrinkage, embrittlement and creep from prolonged tension over time contribute to the weakening of the wood holding the threads in position. This makes for pivot points that are prone to shifting backwards over time or in response to shocks or impacts, resulting in lateral misalignment and unwanted backwards shift of the neck and resulting increase in action.

Instead of movable pivot points, some solutions utilize solid bars glued into the face of headblock. This prevents unequal shifting of the pivot points but further intensifies the stress concentration effect by distributing the stress along a continuous line where the heel is most prone to split and also loses control over the subtle positioning of the neck in forwards or backwards directions to control the vibrating string length. There are also instances where control over the lateral alignment is desirable, particularly with asymmetric instruments such as cutaway guitars that often exhibit unequal deformation on the treble and bass sides of the instrument. In these cases, to compensate for the deformation, some degree of lateral movement needs to be allowable.

Player preference on string distribution across the fingerboard is also a notable concern. Since the bridge is often fixed along the center axis, the lateral angle of the neck controls how the strings are spaced along the fingerboard. Typically the outer strings are placed at equidistant intervals to the fingerboard edge, but depending on playing style this is not always ideal. For players that utilize their thumb to fret bass notes or players that pull the high treble strings downward for note bends or vibrato, their preference would actually be for the bass string to be closer to the edge and the treble string farther from the edge. With movable, independent pivot points, this can be accomplished with a simple adjustment, whereas a bar contact would need to be replaced or reshaped.

The vertical adjustment solution outlined in U.S. Patent Application No. 2007/0107579 exhibits the limitations of added mass due to the extensive headblock and neck heel assemblies and large cutout for the fingerboard extension. Since the design requires additional material to be added to the heel and cut from the upper bout of the instrument, the overall design of the instrument must be redesigned to be built around the dimensions of the neck joint assembly. It also maintains a fixed distance for the vibrating string length so does not allow for changes to compensation to account for body deformation or string gauge changes, nor can the lateral alignment of the neck be adjusted in response to unequal body deformations or user preference to string alignment.

SUMMARY OF THE INVENTION

It is therefore an object of the invention to provide a neck joint that can allow near instantaneous or instantaneous user-control over the neck angle, and hence the string action.

It is another object of the invention to allow for sufficient range of neck angle control to eliminate the need for a neck reset due to deformation from prolonged string tension.

It is another object of the invention to allow for forward or backward shifting of the pivot point to allow for changes to the vibrating string length in order to provide control over string compensation either due to geometric changes from deformation or to accommodate changes in string gauge.

It is another object of the invention to allow for lateral alignment of the neck in response to potential uneven distortion of the instrument body or to purposefully alter the alignment to suit user preferences.

It is another object of the invention to maintain an equivalent impact in terms of weight, gluing surface contact, and overall design and layout on the upper bout of a traditionally-built instrument so that the neck joint can be implemented without excessive deviation from existing designs.

It is another object of the invention to allow for significant rigidity in the assembly to provide tuning pitch and lateral stability without the need for locking screws or additional points of contact that must be engaged.

It is another object of the invention to provide stability against user-applied pull on the neck against the strings.

It is another object of the invention to protect against unwanted movement or failure of the headblock or neck heel due to prolonged string tension or physical shocks and be constructed in such a manner as to allow for easily accessible repairs for all components in the event of damage.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention. A wide variety of potential embodiments will be more readily understood through the following detailed description of certain exemplary embodiments, with reference to the accompanying exemplary drawings in which.

A complete understanding of the present invention may be obtained by reference to the accompanying drawings, when considered in conjunction with the subsequent, detailed description, in which.

For purposes of clarity and brevity, like elements and components will bear the same designations and numbering throughout the Figures.

DETAILED DESCRIPTION OF VARIOUS EMBODIMENTS OF THE INVENTION

Figure 1A:
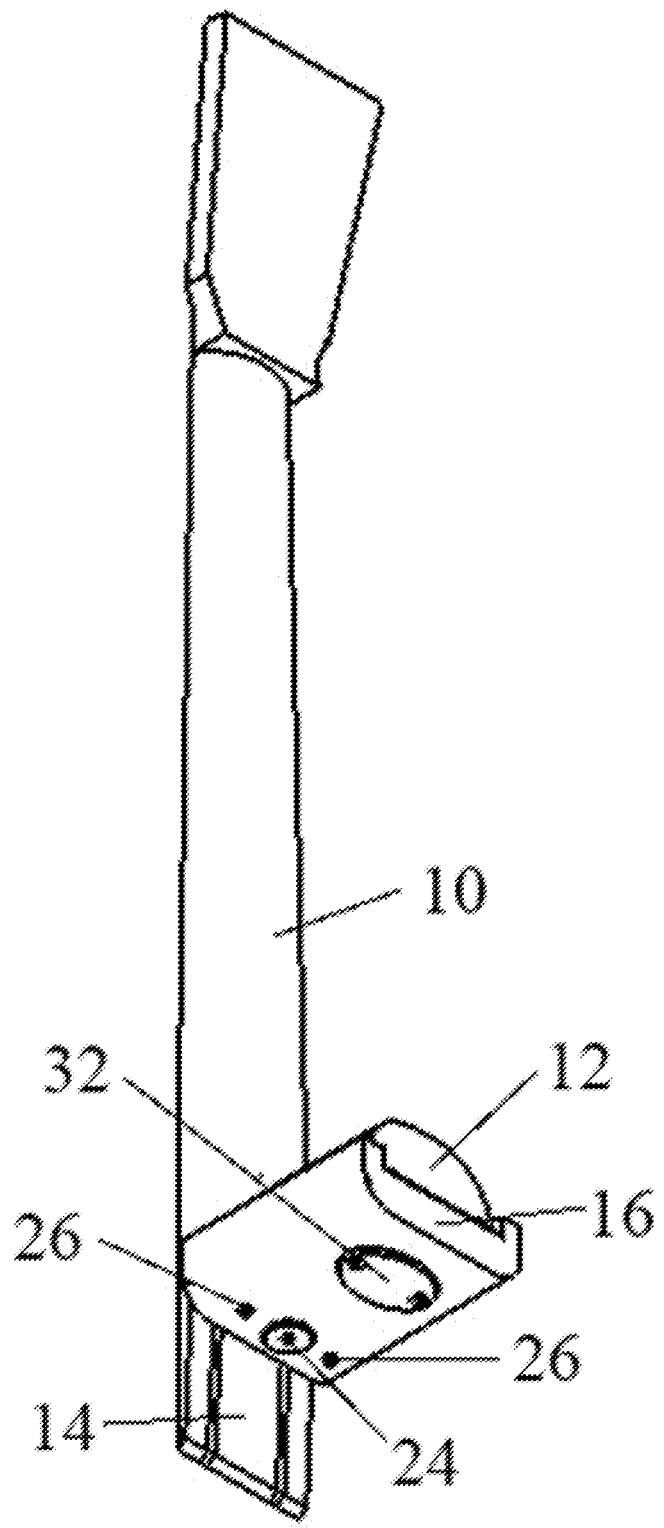
FIG. 1A is a drawing showing a perspective view of the neck joint consisting of a unique neck heel construction and headblock assembly according to an embodiment of the invention.

Apart from the sound production qualities, one of the most important characteristics of a stringed musical instrument is the relative ease of depressing the strings. This characteristic is regulated by the height of the strings above the stopping surface which are either raised metal stops referred to as frets or a straight wooden surface or fingerboard. This height is determined by the angle of the neck relative to the plane of the instrument's face or soundboard and the height of the bridge, which is wooden piece or an assembly that provides physical coupling with the instrument body and a stop for the strings. Both dimensions are largely fixed during the instrument's construction with the neck angle responsible for setting the primary relationship between playing height and bridge height. A smaller factor in playing height is accounted for by a smaller removable piece or saddle, typically $1/8$-$3/16$", in most fixed bridge designs. For bridges of solid wood this amount may be slightly larger (up to $1/4$-$1/2$") but removal or addition is still largely a means of fine tuning instead of establishing playing height.

In the case of fretted instruments, an additional consideration connected with the bridge is fixed intonation. With properly laid out frets, the accuracy of intonation for fretted instrument is dependent on the distance of the string between its two fixed points at the nut on the neck end and the bridge or saddle on the body end, since frets at set distances are calculated from of this string length. Due to the stretching of the strings in the act of fretting, a fretted note is sharper than intended unless this error is mitigated by lengthening the distance between the two fixed points to compensate for the sharpening effect with larger, thicker strings requiring more compensation length than thinner strings. This compensation is created by setting the string length slightly longer than the nominal designed length and by slanting of the bridge/saddle in its slot to account for the differences in string gauge which are typically a 5 or 6-fold difference from thinnest to thickest. Once the bridge is slotted and fixed into position, the only remaining means of control would be to ramp the saddle to fine-tune this compensation, though the degree of adjustment is limited to the thickness of the saddle (typically $3/32$").

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

In accordance with embodiments of the present invention, there is provided an adjustable neck system that seeks to allow for the user to easily and instantaneously or nearly instantaneously adjust string action within a wide range of possible string heights while not impeding on the vibrating area or structural design of the soundboard and adding minimal mass to the headblock assembly and allowing for significant rigidity to allow for greatly improved tuning stability. The system also needs to allow adjustment to the vibrating string lengths in response to intonation compensation requirements. To accomplish this goal a neck joint has been developed utilizing a neck that pivots into a mortised headblock with a floating, cantilevered fingerboard that does not contact the surface of the instrument. The neck heel features extensive reinforcement in conjunction with headblock reinforcement to allow for increased torque and thus greater normal force between the neck heel and pivot points for greater rigidity and stability without the need for locking screws. This normal force is provided by a bolt colinear with the pivot points that utilizes a conical spring washer to maintain tension while allowing the bolt to deviate from a perpendicular axis relative to the headblock in response to changes in neck angle. The heel is reinforced with a vertically-oriented bar of, in a preferred embodiment, carbon fiber set in the heel with the tallest dimension parallel and collinear with the pivot screws and a backing vertically-oriented strip of carbon fiber centered and perpendicular to the preceding bar to stabilize and distribute the stress at the point of contact. In one aspect, the headblock is reinforced with a conical insert of endgrain hardwood glued into the headblock with a flanged, threaded insert seated at the center of the hardwood cone. By laminating the headblock with the grain at alternating right angles and cantilevering the fingerboard, traditional dimensions can be maintained without risk of splitting so that mass and soundboard contact area are not significantly greater than with traditional assemblies for minimal effect on weight balance and tone. Use of a threaded insert embedded in the heel and a captive plate at the headblock provide additional stability to counter backwards pull of the neck by the a user. All gaps between the neck and the body of the instrument are lined at the body with a compressible material that provides a seal while still allowing for free movement. In aspects, the compressible material is easily compressible.

Figure 1B:
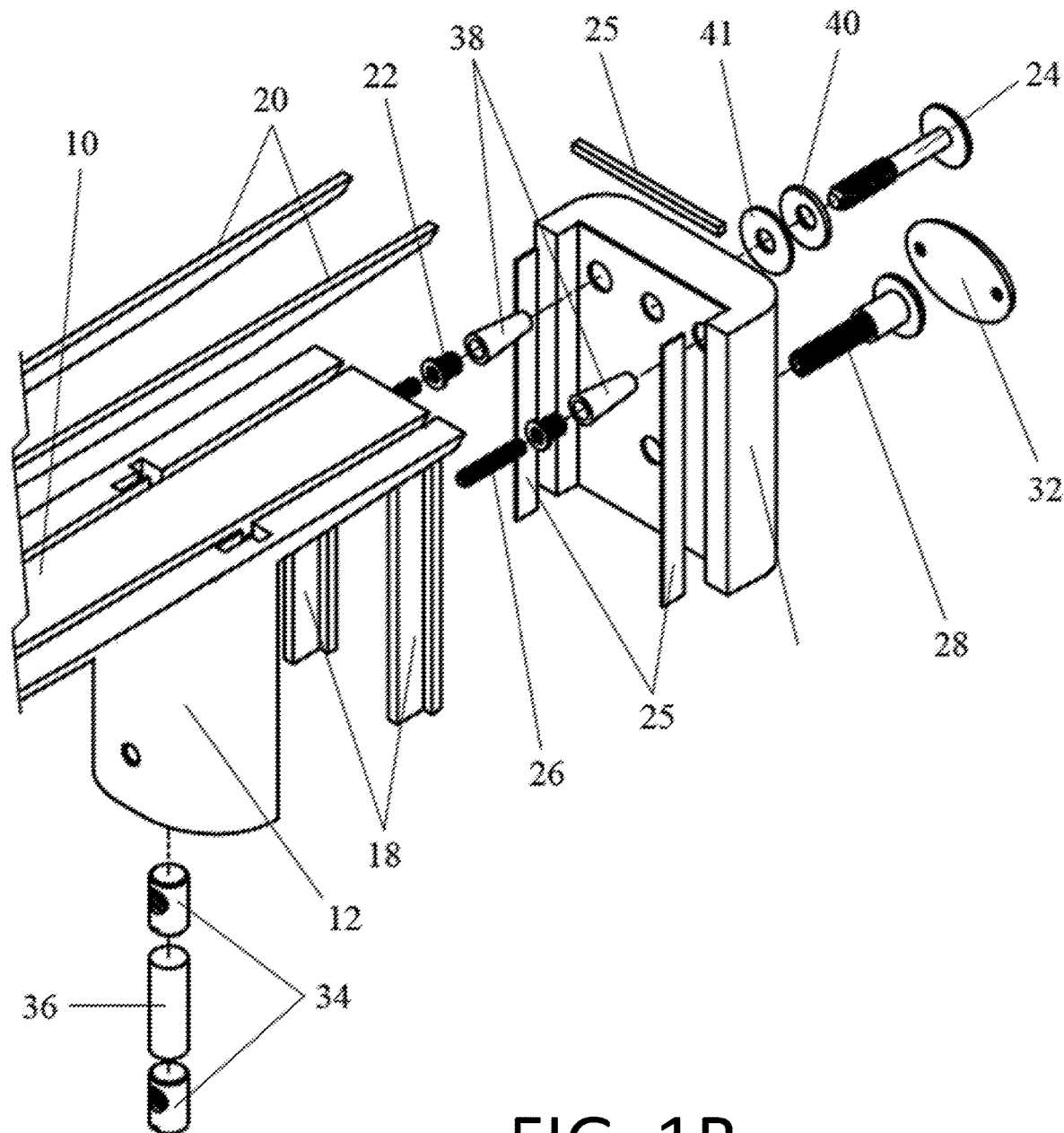
FIG. 1B is a drawing showing an exploded view which displays the individual components of the neck, heel, and headblock assemblies according to an embodiment of the invention.

FIG. 1A is a perspective view of the neck 10 joint consisting of a unique neck 10 heel 12 construction and headblock 16 assembly. It shows the neck nested into a mortise cut into the headblock. The view shows the headblock as seen from the interior of the instrument which is the main point of access for adjusting the pivot set screws 26, tightening or loosening the coupling bolt 24, and removing the retaining plate 32 and adjustment bolt 28 if needed for repair. FIG. 1B is an exploded view of the assembly revealing each component of the design.

Figure 2:
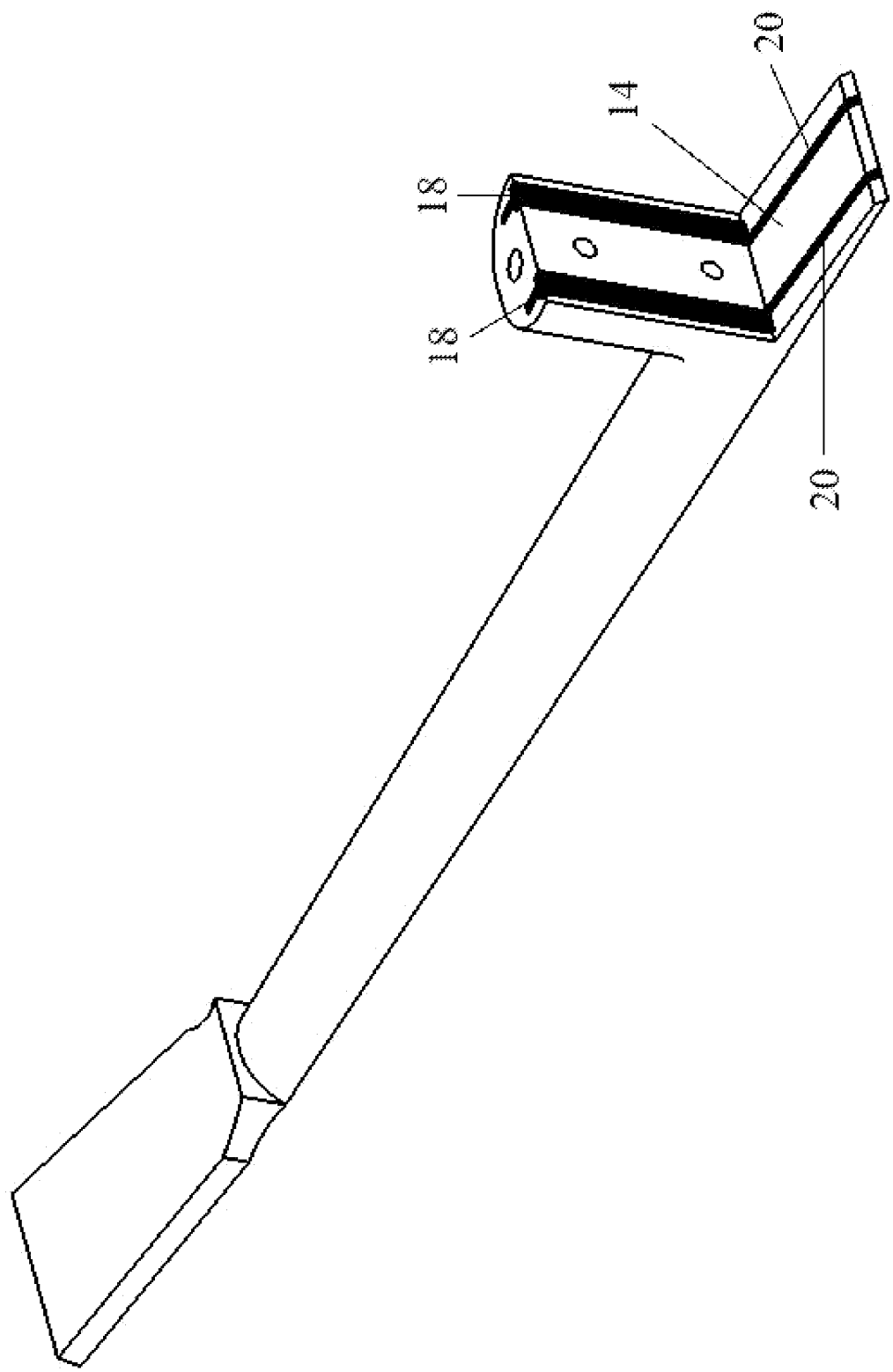
FIG. 2 is a drawing showing a perspective view of a neck heel as seen from the plane of contact with the headblock according to an embodiment of the invention.

FIG. 2 is a perspective view of a neck heel as seen from the plane of contact with the headblock. This shows the t-section heel reinforcements 18 which bear the contact point of the set screws. The t-section provides sufficient surface area at the plane of contact to distribute the concentrated stresses of the pivot points while also presenting an elongated neutral axis for enhanced stiffness against any bending moment. The neck reinforcement bars 20 are also seen supporting the underside of the tapered fingerboard extension 14 with sufficient stiffness so that the neck can be cantilevered for freedom of movement without collision with the top.

Figure 3:
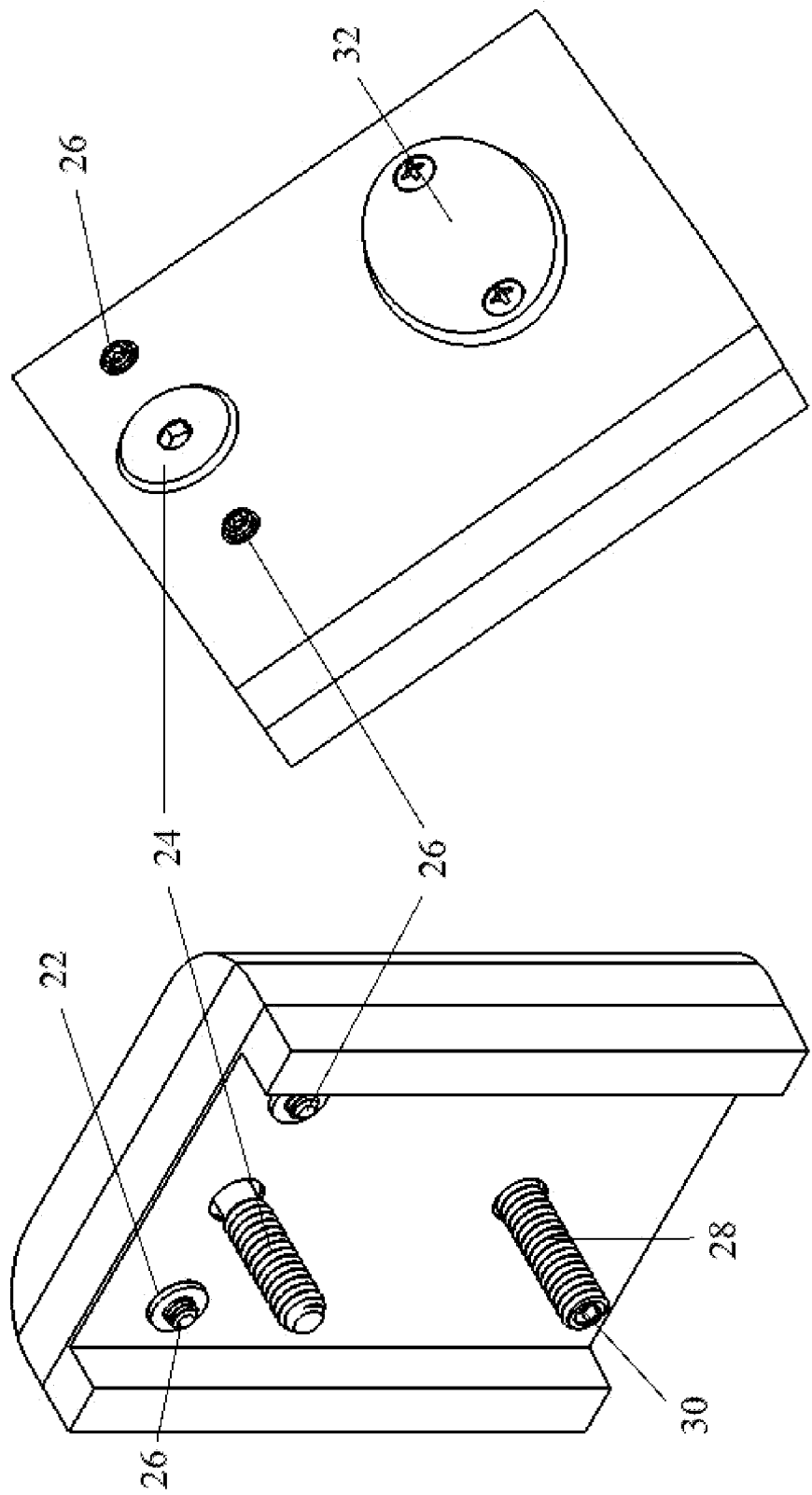
FIG. 3 is a drawing showing a perspective view of the headblock assembly from both the contact plane and interior surface according to an embodiment of the invention.

FIG. 3 is a set of opposite perspective views of the headblock. At the contact plane the pivot of the neck is established by a pair of pivot set screws 26 at equidistant points in a perpendicular line to the vertical axis of the neck heel. Flanged threaded inserts 22 fix the tracking axis for the set screws. Adjustment of either the horizontal displacement or yaw of the neck by pitching the screws forwards or backwards is controlled by means of Allen wrenches from the inside of the instrument. While string tension holds the adjustment bolt 28 against the surface of the headblock, any moment in the opposing direction can separate contact from the pivot point or significantly alter pitch if the adjustment bolt is unrestrained so a retaining plate 32 is screwed into the headblock with moderate spring tension against the head of the adjustment bolt 28. The spring tension of the plate allows for the very slight changes in the angle of the adjustment bolt 28 with any corresponding changes in neck angle. While the bolt head is covered from the interior, the user will be able to turn the adjustment bolt 28 by means of the Allen socket adjustment 30 at the tip through an adjustment access hole that runs through to the exterior of the heel.

Figure 4:
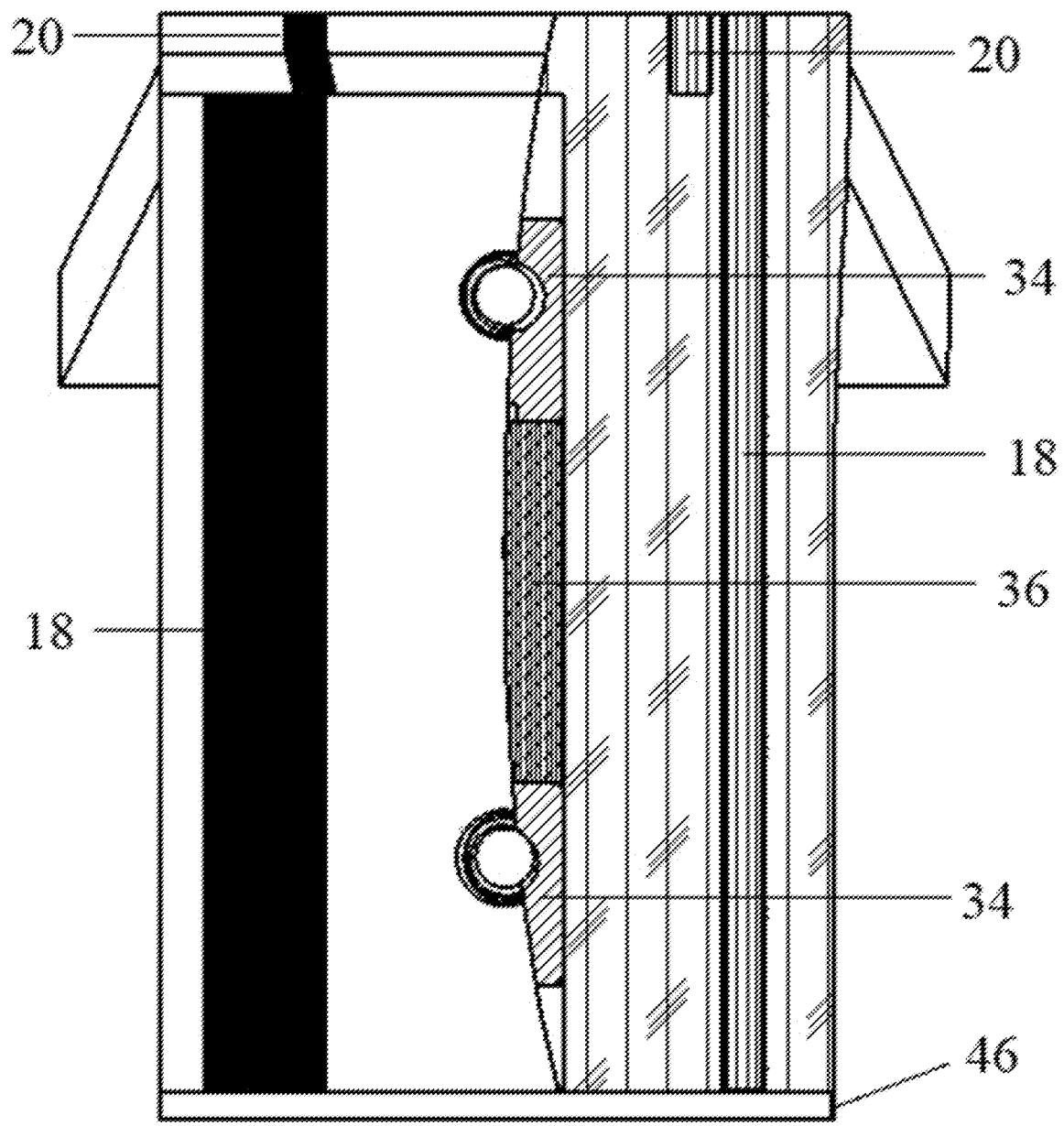
FIG. 4 is a drawing showing a front sectional view of the neck heel construction showing part of the heel reinforcement and threaded inserts for the coupling and movement of the neck according to an embodiment of the invention.

FIG. 4 is a front sectional view of the neck heel construction showing a cross-section at the centerline detailing the heel support structure. By using barrel-shaped threaded inserts 34 that are inset into matching cylindrical channels in the neck, this arrangements mitigates the relatively weak endgrain of the heel wood. Reinforcing dowels 36 are added between the two inserts and filling further spaces to replace lost material in the act of drilling. This adds further reinforcement although the t-section heel reinforcements provide primary strength and stiffness through the heel. In the event of damage to the insert or its threads, the inserts can be drilled out and extracted through the bottom of the heel with cosmetic repairs limited to replacing the heel cap veneer 46 and associated finish touch-up.

Figure 5A:
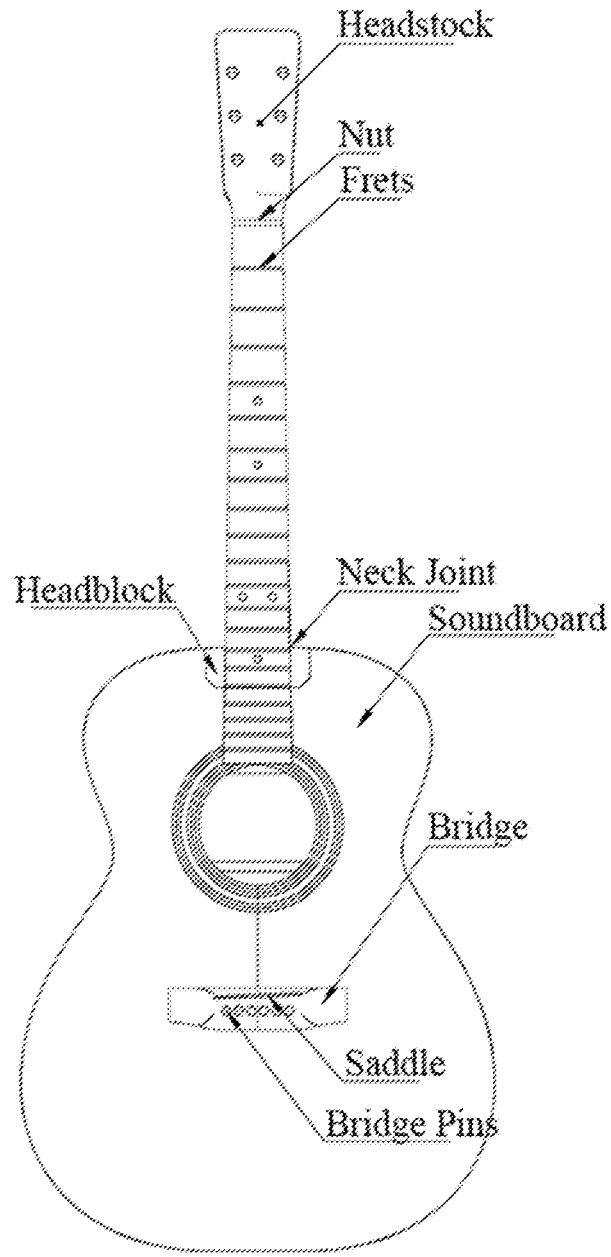
FIG. 5A is a drawing illustrating the various components of a typical stringed instrument as described herein.
Figure 5A:
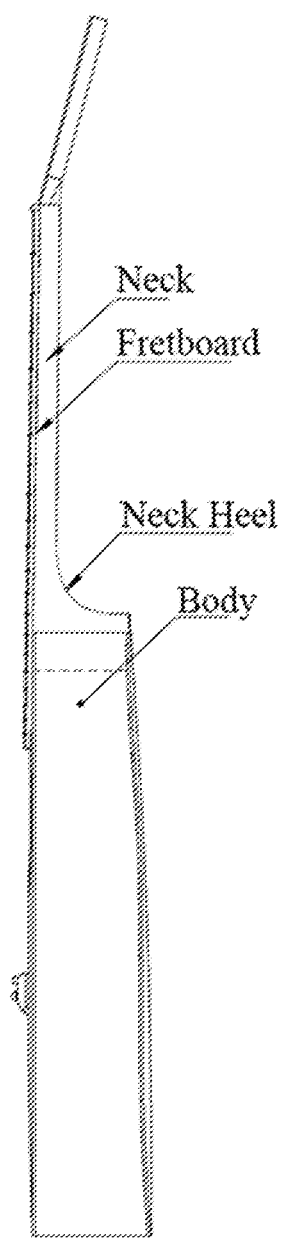
Figure 5B:
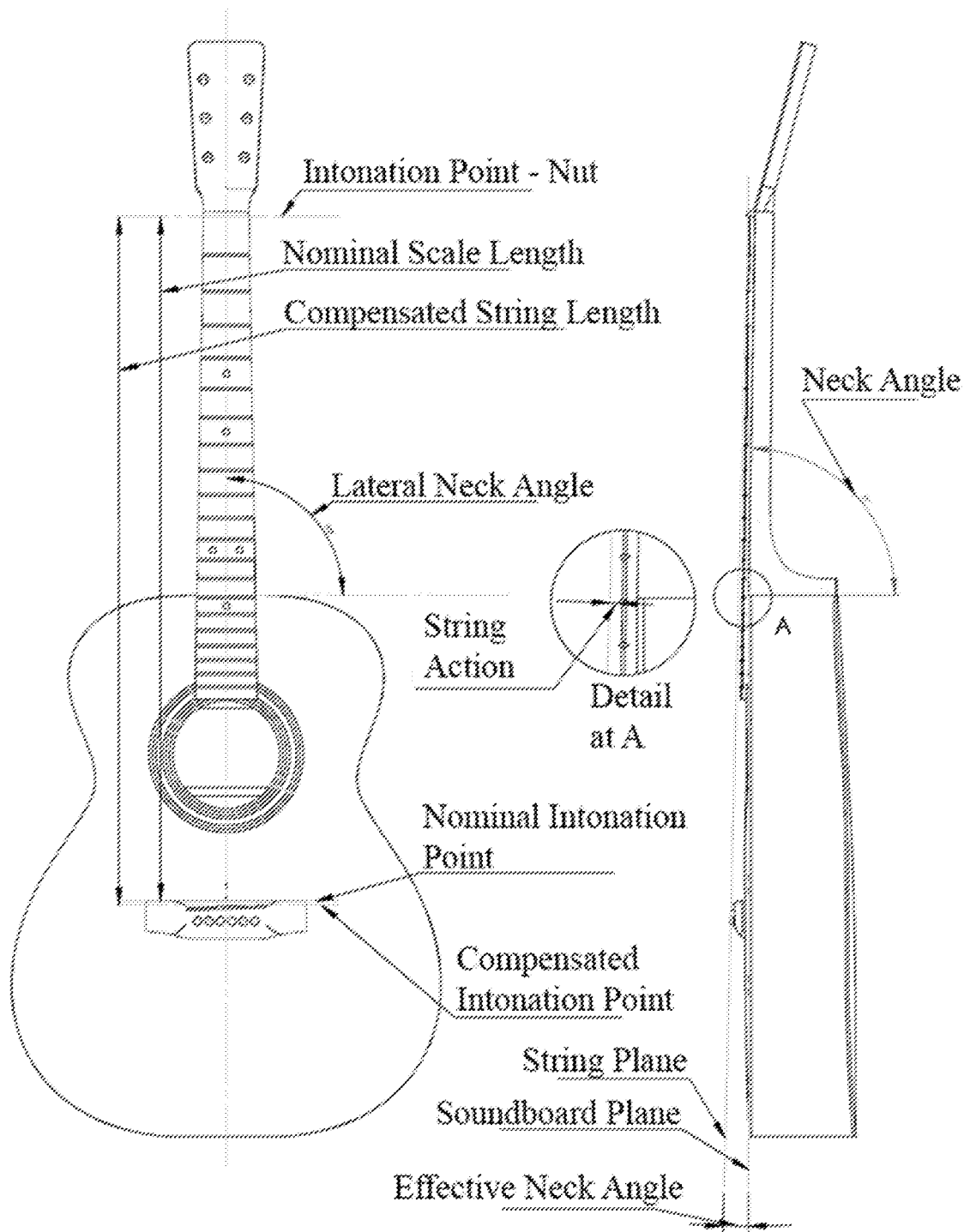
FIG. 5B is a drawing showing exemplary dimensions and angles that are referenced herein.
Figure 5C:
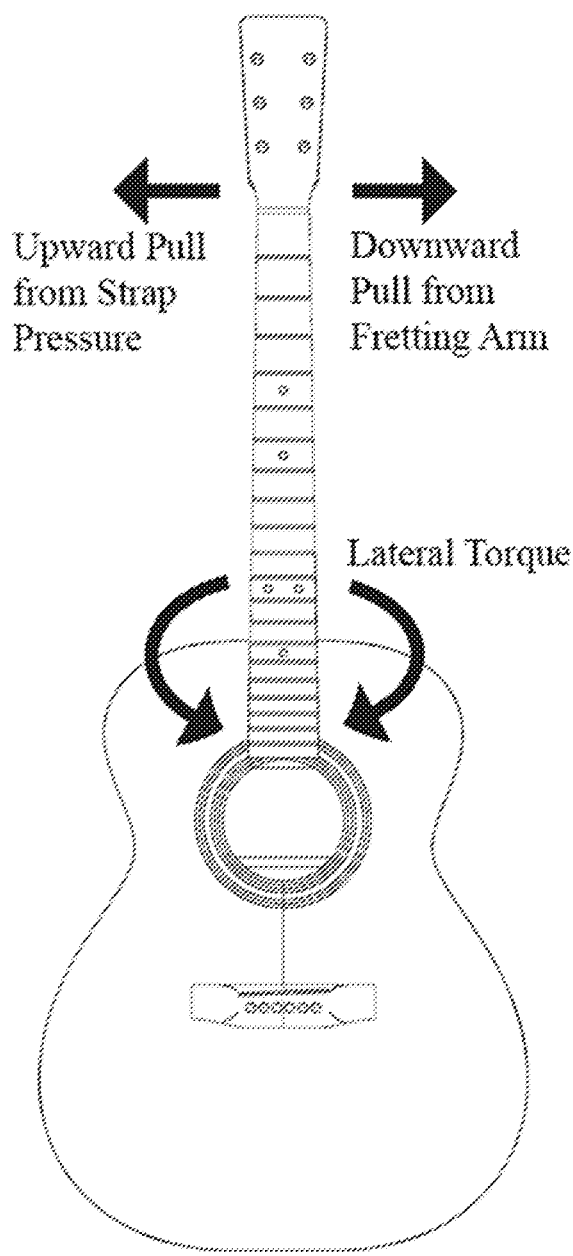
FIG. 5C is a drawing that outlines the principal forces under consideration herein.
Figure 5C:
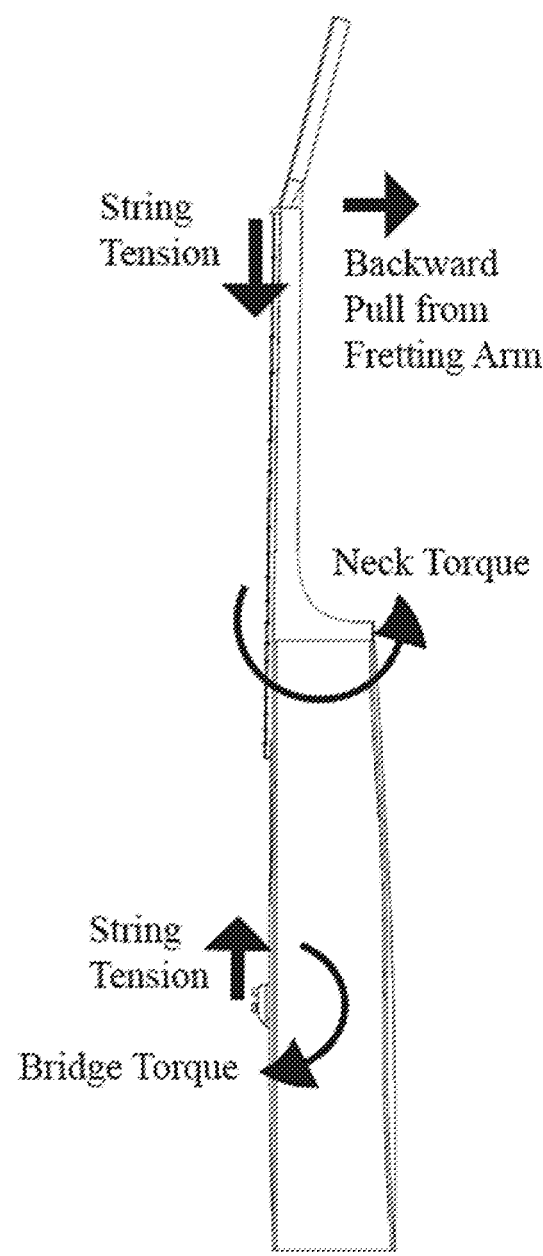
Figure 5D:
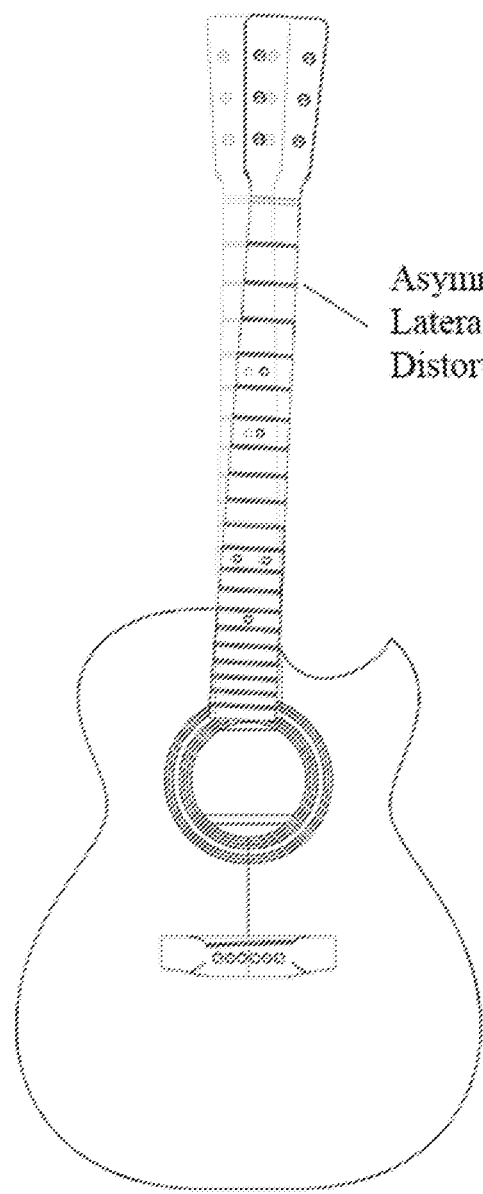
FIG. 5D is a drawing that outlines the principal forces under consideration herein.
Figure 5D:
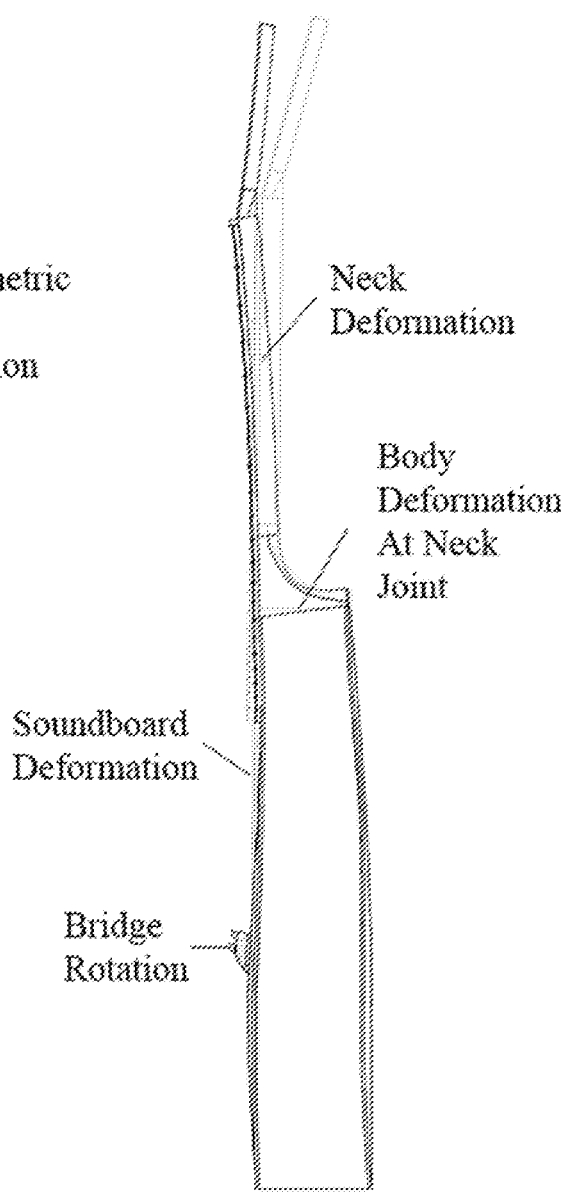

FIG. 5A is a picture illustrating the various components of a typical stringed instrument as described herein. For example, in one aspect of the instrument, the instrument has a headstock, nut, frets, neck joint, soundboard, bridge saddle, bridge pins, neck, fretboard, neck heel, and body. FIG. 5B is a diagram showing exemplary dimensions and angles that are referenced herein, including neck angle and others that are influenced by the disclosed invention. FIG. 5C is a figure that outlines the principal forces under consideration herein, including upward, downward, forward, and backward pull on the neck, as well as lateral, neck, and bridge torque. FIG. 5D is another figure that outlines the principal forces under consideration, showing how the neck and body are deformed under certain conditions as described herein.

Figure 6:
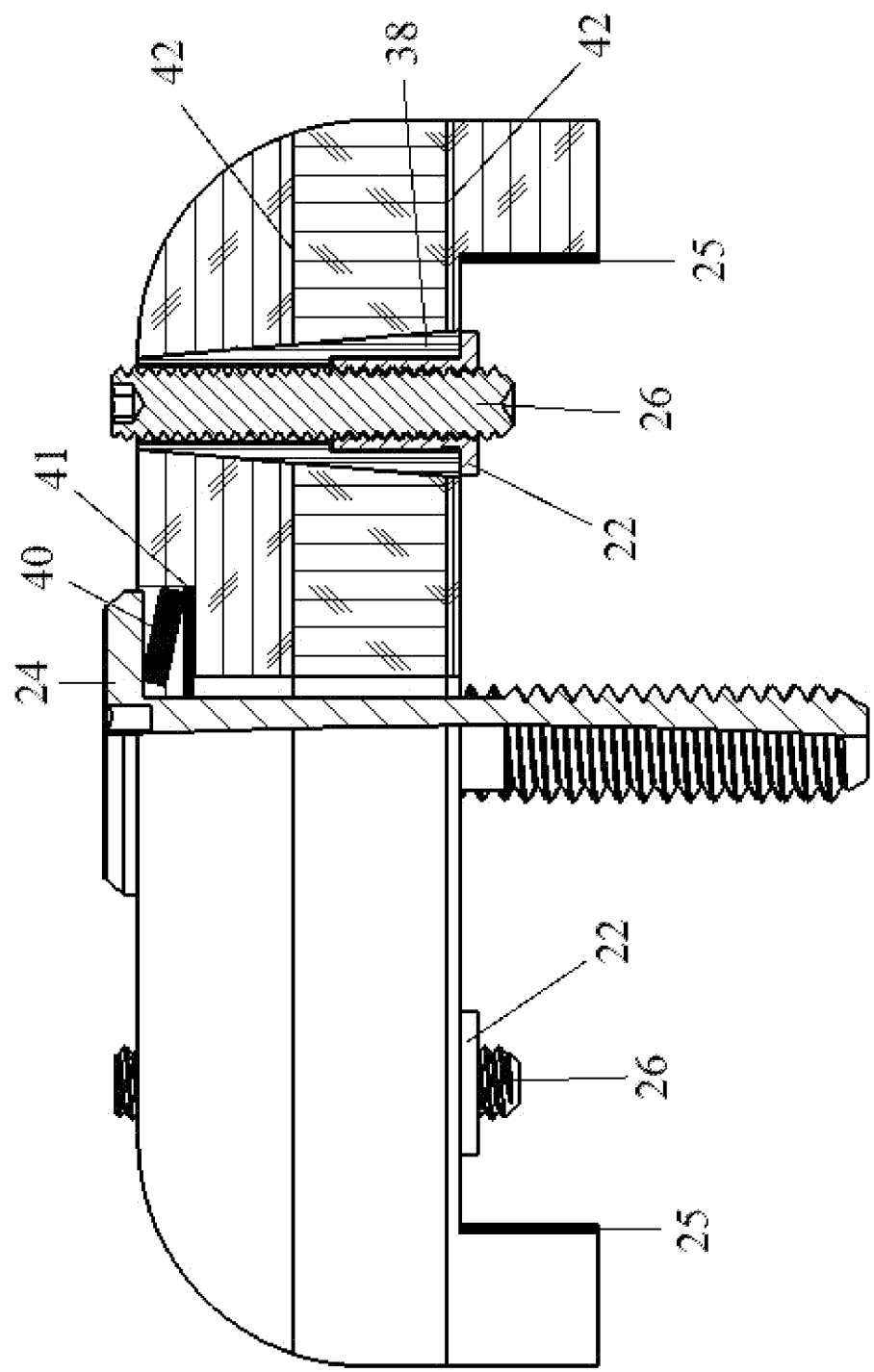
FIG. 6 is a drawing showing a top sectional view of the headblock with a cross section at the pivot point according to an embodiment of the invention.

FIG. 6 is a top sectional view of the headblock 16 with a cross section at the pivot point. In order to provide enough support for enhanced tension with the coupling bolt 24, a number of reinforcements have to be made to the headblock to achieve sufficient strength and stiffness. Headblock laminations 42 with opposing grain directions prevents the likely occurrence of splitting due to the concentrated stresses and removes the need for added surface area as a solution to adding strength. Instead of relying on the compression strength of wood grain perpendicular to normal force, a conical plug 38 of dense hardwood (i.e. Ebony) is glued into place before flanged inserts 22 are set into position. The conical shape prevents long-term creep of the glue joint and presents endgrain wood in compression which offers superior strength to the face-grain headblock wood. The flange on the inserts ensure that the superior compressive strength of the endgrain hardwood inserts ensure the pivot screws remain fixed. While the insert only covers a partial length of the set screw's threads, the conical insert is threaded to accept the set screws, providing additional contact and support to keep the screws aligned on-axis as well as provide sufficient friction to prevent unwanted rotation of the screw. A conical washer 40 is used between the headblock and coupling bolt 24 so that the washer can bear the increased bolt tension instead of the wood bearing the compression and generating uneven tension around the bolt head. A flat washer 41 between the conical washer and the headblock distribute the otherwise concentrated stress around the outside edge of the conical washer to avoid local deformation of the headblock. The sides of the headblock mortise are cut slightly larger than the width of the heel with the resulting gap filled by a lining 25 of felt, cork, or other compressible, non-marring material. The relatively free movement of the material provides a seal to prevent moisture and debris from contaminating the joint while allowing enough clearance for the adjustment of the neck to rotate unimpeded.

Figure 7:
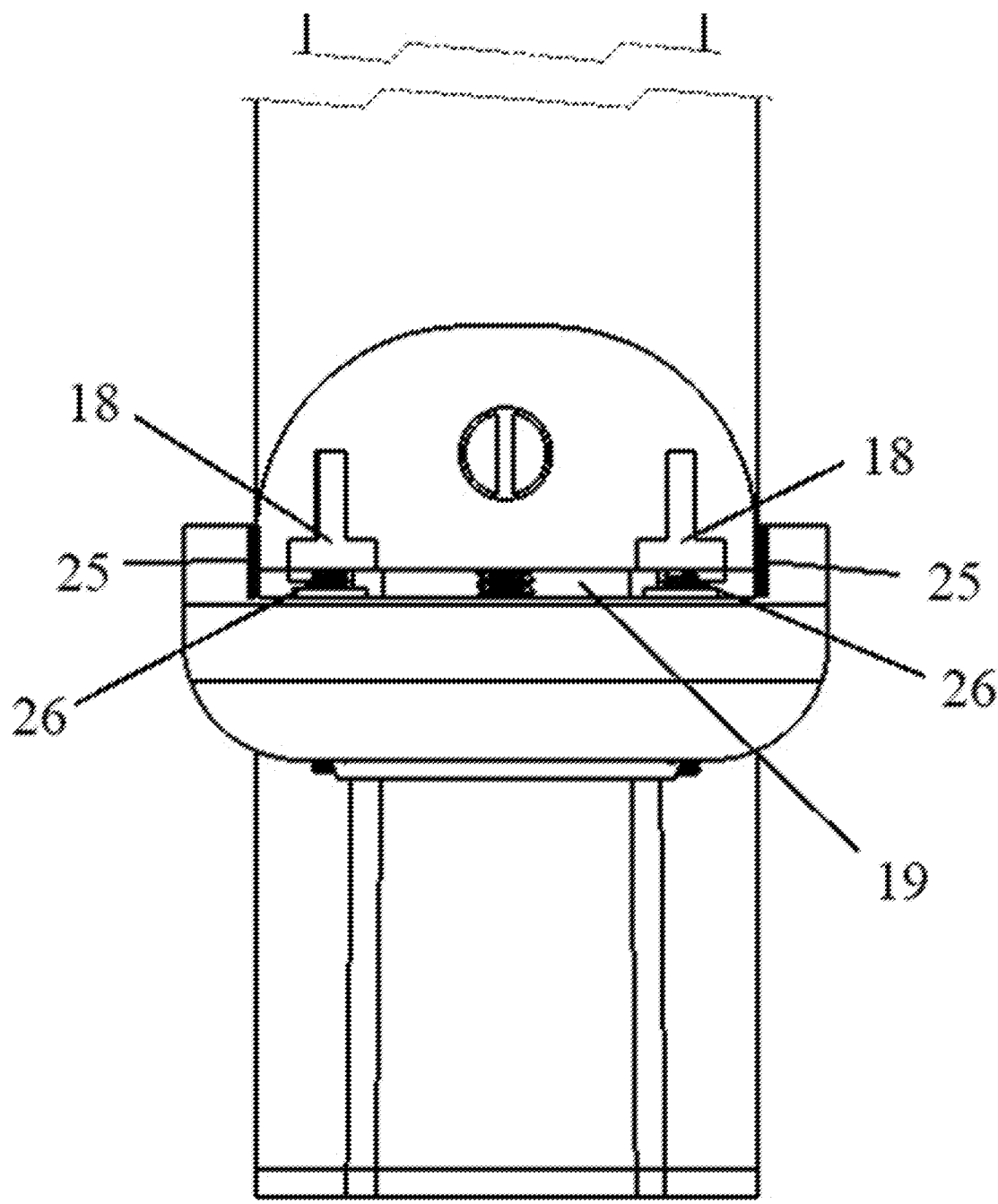
FIG. 7 is a drawing showing a bottom view of the neck joint in position according to an embodiment of the invention.

FIG. 7 is a bottom view of the neck joint in position. The gap 19 between the headblock and the heel allow for the significant range of motion in neck angle as well as allow for future extension or retraction in the distance of the pivot point in response to body deformation or as a means of changing the string compensation in response to string gauge changes. The view shows the ideal axial alignment of the pivot point 26 and the long flange of the T-section heel reinforcement 18 but also the extended bearing surface in the event of any misalignment of mating parts. The lining 25 between the interface of the parts is shown as well.

Figure 8:
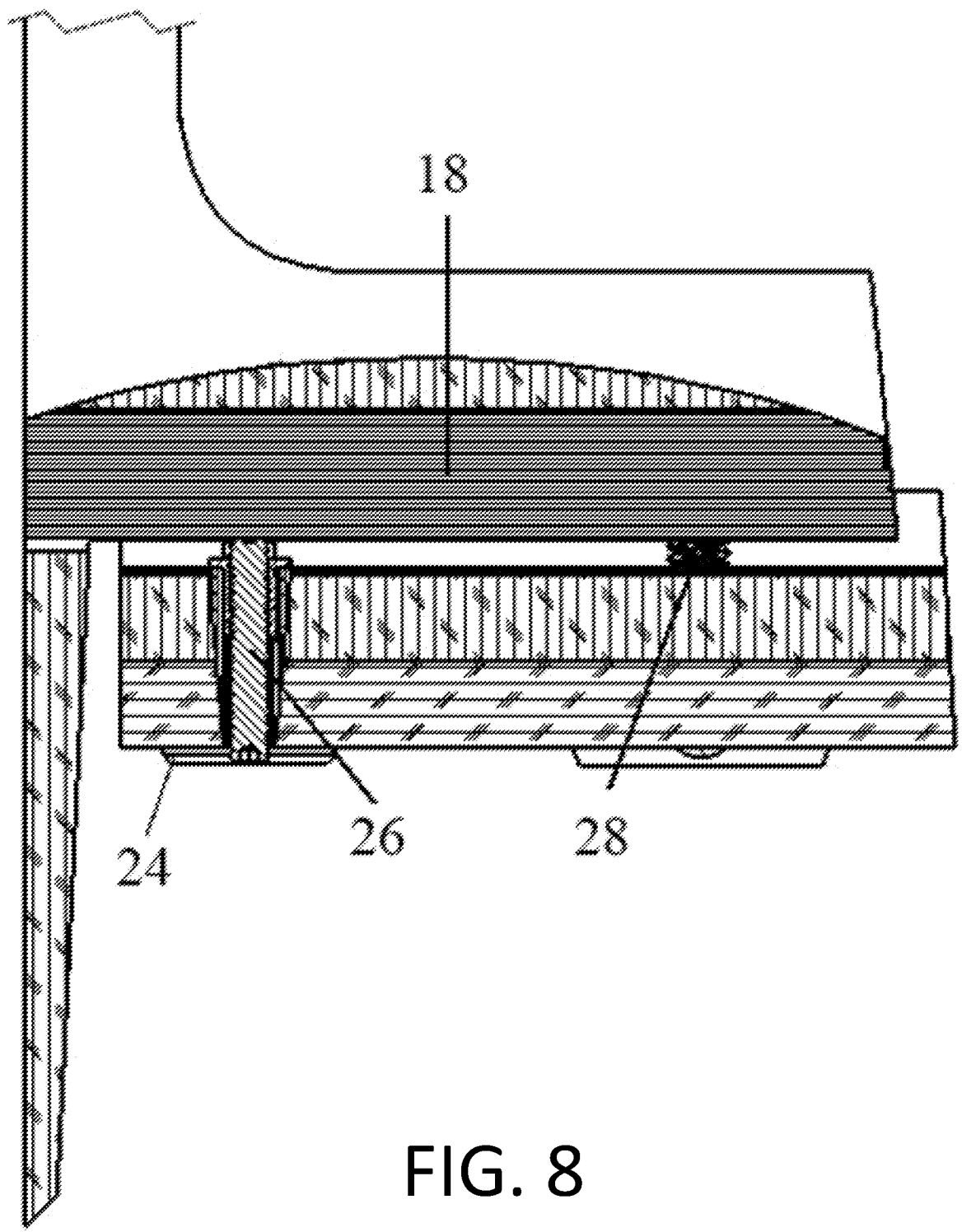
FIG. 8 is a drawing showing a right sectional view of the neck joint with cross-section at the right pivot point according to an embodiment of the invention.

FIG. 8 is a right sectional view of the neck joint with cross-section at the right pivot point, showing the considerable length of t-section carbon-fiber composite heel reinforcement 18 acting in counter to the normal force of the pivot set screw 26 and the moment from string tension about the pivot point and the adjusting bolt 28. The long (in aspects, carbon-fiber) bar parallel to the pivot screws provides stiffness against the shear induced by the pivot assembly while maintaining a small cross section to prevent excessive sonic damping and sufficient surface area for a strong glue joint. The strength of this cross-section enables the heel assembly to safely receive the ordinary forces stemming from string tension and torque on the heel as well as increased forces from the added tension through the coupling bolt 24 as well as short-term dimensional stability, long-term resistance to deformation over time, and protection against impacts and shocks.

Figure 9:
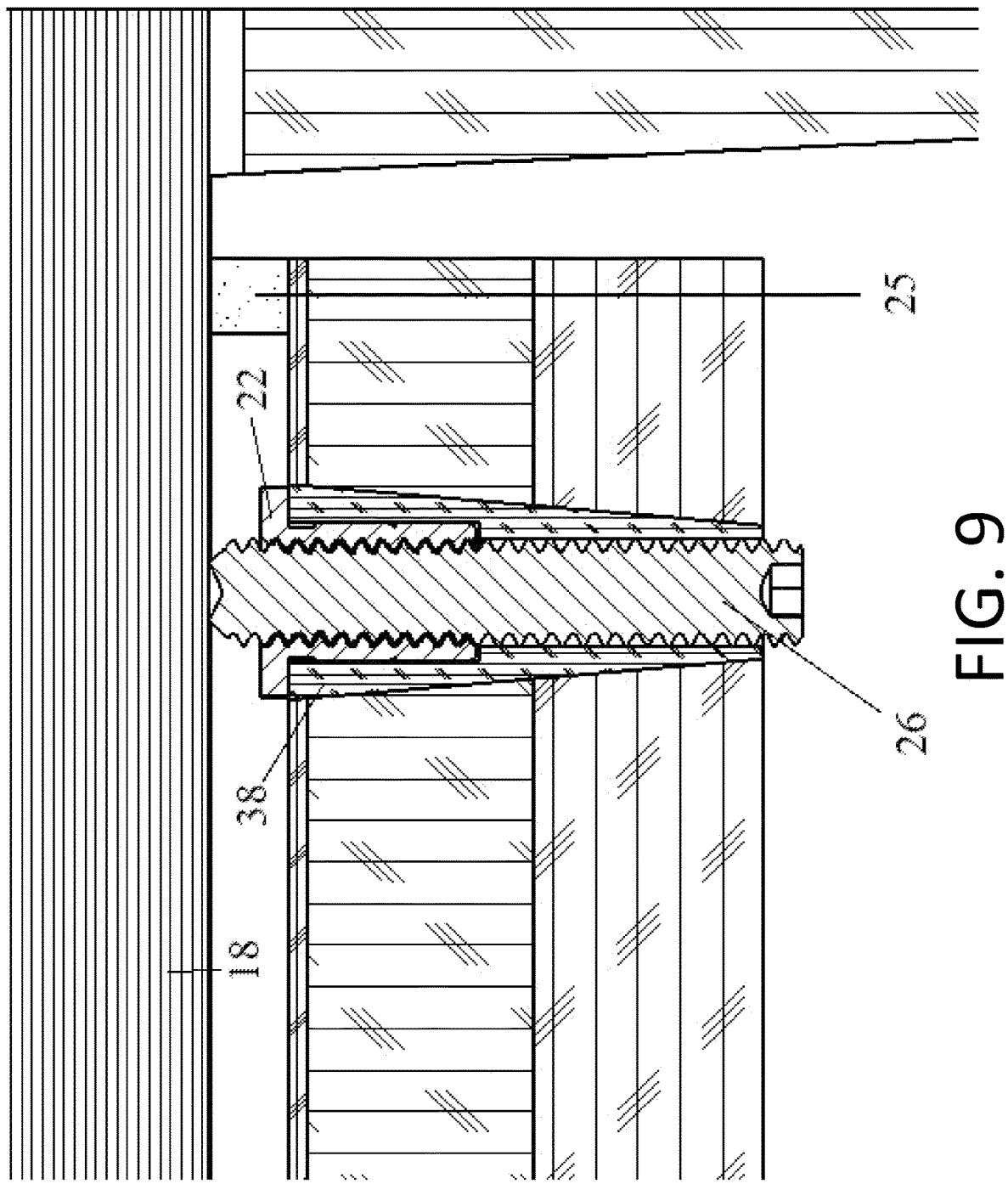
FIG. 9 is a drawing showing a detail view of the pivot point of the assembly according to an embodiment of the invention.

FIG. 9 is a detail view of the pivot point of the assembly with a closer look at the relationship between the contact point between the headblock and neck heel. In particular, this view details the relationship between the conical plug 38, pivot screw 26, flanged insert 26, and headblock. The view also shows the sealing strip 25 of cork, felt, or other compressible material that covers the gap between the heel and headblock.

Figure 10:
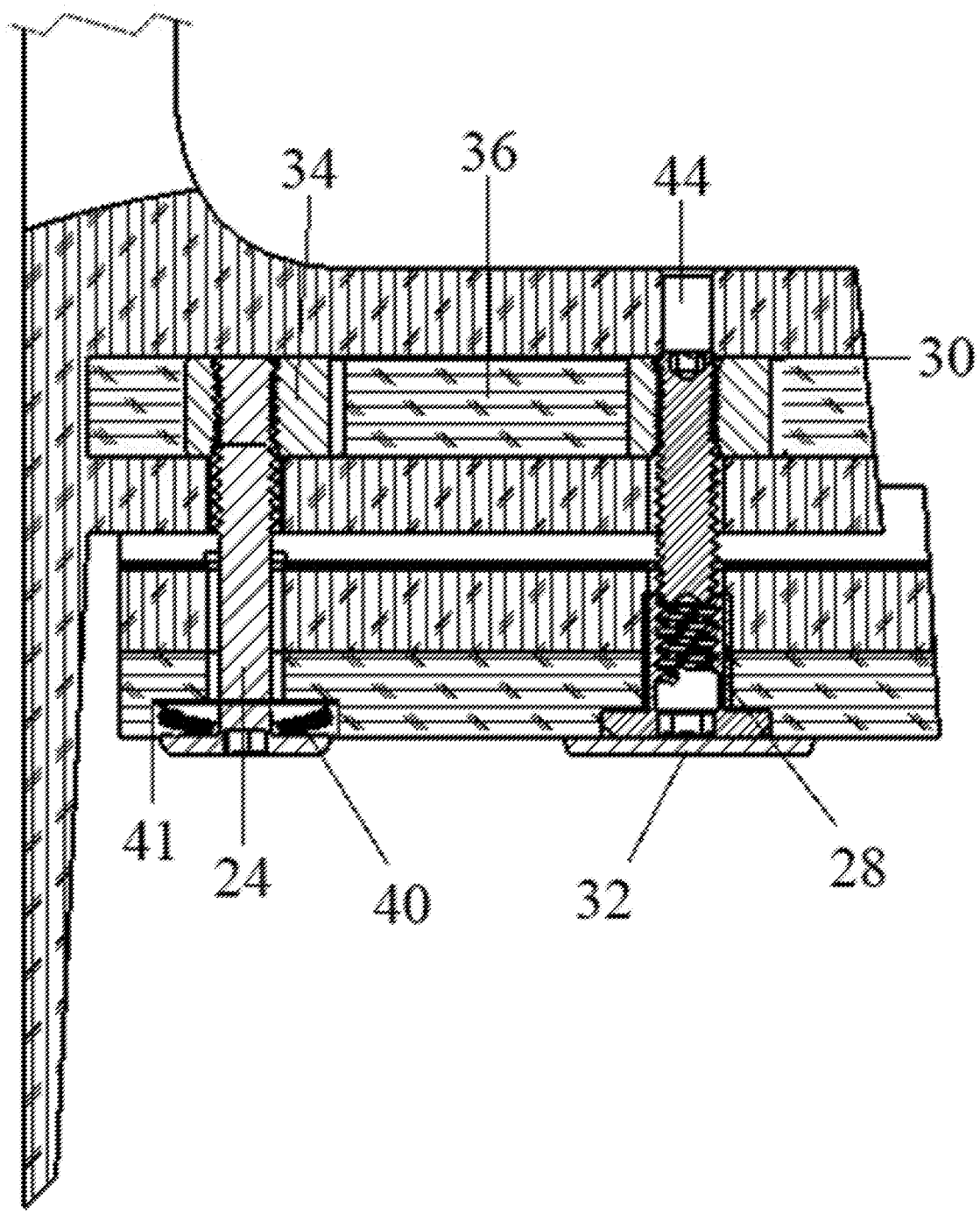
FIG. 10 is a drawing showing a section view of the neck assembly at the midpoint of the coupling bolts according to an embodiment of the invention.

FIG. 10 is a cross-section view of the neck and heel assembly taken at the midpoint of the coupling bolts. The connections between the bolts and captive threaded inserts in the heel are illustrated in more detail as well as the point of end-user adjustment through the adjustment access hole 44. The embedded point of access ensures that no accidental movement of the adjustment bolt occurs and minimizes the visual impact and number of glue joints that can telegraph through finishes from differential expansion.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A musical instrument adjustable neck joint comprising:
   lengthwise neck reinforcement bars providing stiffness and dimensional stability for a neck shaft and fingerboard extension;
   pivot set screws establishing pivot points from which the neck can rotate to establish a neck angle with control over lateral alignment; and
   an adjustment bolt providing neck angle adjustment by adjusting a length or distance of a gap between a neck and a body of the instrument.

2. The musical instrument adjustable neck joint of claim 1, further comprising a coupling bolt capable of drawing the neck into contact with the pivot points to stabilize the neck.

3. The musical instrument adjustable neck joint of claim 1, wherein the adjustment bolt is capable of adjustment by way of an adjustment tool.

4. The musical instrument adjustable neck joint of claim 1, further comprising a retaining plate capable of providing pressure to prevent unwanted movement in a bending moment counter to a string pull.

5. The musical instrument adjustable neck joint of claim 1, further comprising threaded barrel inserts capable of providing grip and tracking for the coupling and adjusting bolts.

6. The musical instrument adjustable neck joint of claim 1, further comprising a central reinforcement capable of strengthening the heel after clearing lost material due to drilling the threaded inserts.

7. The musical instrument adjustable neck joint of claim 1, further comprising a plug capable of providing a surface for flanged threaded inserts to prevent long-term deformation of headblock wood.

8. The musical instrument adjustable neck joint of claim 1, further comprising a washer capable of providing tension in the coupling bolt and neck assembly.

9. The musical instrument adjustable neck joint of claim 1, further comprising headblock laminations in alternating right angles of grain direction, which headblock laminations are capable of providing sufficient strength and resistance to splitting to withstand added tension from the coupling bolt and pivot points while maintaining headblock dimensions.

10. The musical instrument adjustable neck joint of claim 1, further comprising an adjustment access opening capable of enabling user control of the neck adjustment.

11. The musical instrument adjustable neck joint of claim 1, further comprising a set of linings and strips capable of providing a seal between the neck and body.

12. The musical instrument adjustable neck joint of claim 1, further comprising t-section heel reinforcements comprising carbon-fiber composite.

13. The musical instrument adjustable neck joint of claim 1, wherein the lengthwise neck reinforcement bars comprise carbon-fiber composite.

14. The musical instrument adjustable neck joint of claim 3, wherein the adjustment tool is an Allen wrench.

15. The musical instrument adjustable neck joint of claim 7, wherein the plug is a conical plug.

16. The musical instrument adjustable neck joint of claim 7, wherein the surface for the flanged threaded inserts to prevent long-term deformation of the headblock wood is a flush surface.

17. The musical instrument adjustable neck joint of claim 7, wherein the flanged threaded inserts comprise dense hardwood endgrain.

18. The musical instrument adjustable neck joint of claim 8, wherein the washer is a conical washer.

19. The musical instrument adjustable neck joint of claim 8, wherein the washer is a flat washer.

20. The musical instrument adjustable neck joint of claim 10, wherein the adjustment access hole is dimensioned to fit an Allen wrench.

21. The musical instrument adjustable neck joint of claim 11, wherein the set of linings and strips capable of providing a seal between the neck and body are comprised of a compressible, non-marring material.

* * * * *